US00PP10877P

United States Patent [19]

Parsons

[11] Patent Number: Plant 10,877

[45] Date of Patent: May 4, 1999

[54] SCAEVOLA PLANT NAMED 'SUNFAN'

[75] Inventor: Rodney James Parsons, Hoddles Creek, Australia

[73] Assignee: Outeniqua Nursery, Emerald, Australia

[21] Appl. No.: 08/977,922

[22] Filed: Nov. 24, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Melissa L. Kimball
*Attorney, Agent, or Firm*—C. A. Whealy

[57] ABSTRACT

A distinctive cultivar of Scaevola plant named Sunfan, characterized by its compact and upright plant habit; dense and bushy plant form and freely branching plant habit; long flowering cycle and small light violet blue fan-shaped flowers.

2 Drawing Sheets

The present invention relates to a new and distinct cultivar of Scaevola plant, botanically known as *Scaevola aemula* and referred to by the cultivar name Sunfan.

The new Scaevola was discovered by the inventor in a controlled environment in Hoddles Creek, Victoria, Australia, in early 1994, as a naturally-occurring mutation of a selection of *Scaevola aemula*, inventor's code number 345/94. The new Scaevola was observed as a single plant that was more compact and upright and differed in flower color.

Asexual reproduction of the new cultivar by stem and terminal cuttings taken in Hoddles Creek, Victoria, Australia, has shown that the unique features of this new Scaevola are stable and are reproduced true to type in successive propagations.

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Sunfan' which distinguish 'Sunfan' as a new and distinct cultivar:

1. Compact and upright plant habit.
2. Dense and bushy plant form and freely branching plant habit.
3. Long flowering cycle.
4. Small light violet blue fan-shaped flowers.

Plants of the new Scaevola can be compared to plants of the *Scaevola aemula* cultivar Petite Wonder (not patented), however plants of these two cultivars differ in the following characteristics:

1. Plants of the new Scaevola are denser and more upright in plant habit than plants of the cultivar Petite Wonder.
2. Plants of the new Scaevola are more vigorous than plants of the cultivar Petite Wonder.
3. Plants of the new Scaevola have leaves that are lighter green in color and have larger and more numerous serrations.
4. Plants of the new Scaevola have longer flowering cycle than plants of the cultivar Petite Wonder.
5. Plants of the new Scaevola have larger and lighter violet blue flowers than plants of the cultivar Petite Wonder.

BRIEF DESCRIPTION OF THE PHOTOGRAPHS

The accompanying colored photographs illustrate the overall appearance of the new cultivar, showing the colors as true as it is reasonably possible to obtain in colored reproduction of this type.

The photograph on the first sheet comprises a top perspective view of a typical hanging basket plant of 'Sunfan'.

The photograph on the second sheet comprises a close-up view of typical flowers of plant of 'Sunfan'. Flower and foliage colors in the photographs may appear different from the actual colors due to light reflectance.

DETAILED BOTANCIAL DESCRIPTION

The following observations and measurements describe plants grown during the spring and summer in Encinitas, Calif. under full sun with day and night temperatures averaging 24° and 16 C., respectively. Color references are made to The Royal Horticultural Society Colour Chart except where general terms of ordinary dictionary significance are used.

Botanical classification: *Scaevola aemula* cultivar Sunfan.

Parentage: Naturally-occurring mutation of a selection of *Scaevola aemula*, inventor's code number 345/94.

Propagation:

*Type cutting.*—Stem and terminal cuttings.

*Time to initiate and develop roots.*—Summer: About 11 days at temperatures of 20 to 25° C. Winter: About 24 days at temperatures of 20 to 25° C.

*Rooting habit.*—Numerous and fine.

Plant description:

*Plant form.*—Upright, to about 30 cm, but as stems elongate plants become more spreading. Suitable for hanging basket containers.

*Growth habit.*—Moderately vigorous and freely branching, dense and bushy.

*Stem description.*—Form: Indeterminate. Internode length: About 1.3 cm. Diameter: About 2 mm. Color: 144A. Texture: Smooth with very fine pubescence.

*Foliage description.*—Arrangement: Alternate, single. Size: Length: About 3.5 cm. Width: About 1.75 cm. Shape: Spatulate. Tip: Cuspidate. Base: Attenuate. Margin: Irregularly serrated, becoming more serrated towards leaf apex. Texture: Fine pubescence, dull, somewhat leathery. Color. Upper surface: Greener than 146A. Lower surface: Greener than 146B.

Flower description:

*Flower type and shape.*—Semi-circular, fan-shaped flowers with five petals fused at the base to form a tubular flower throat. Flowers persistent and flowering continuous. In Encinitas, Calif., plants were in full bloom from mid-March to mid-September.

Flower throat open along the upper surface exposing reproductive organs. Flowers persistent.

*Flower arrangement.*—Flowers arise from leaf axils with one flower per axil.

*Perianth.*—Aspect: Fan-shaped, flat. Length: About 1.5 cm. Diameter: About 1.5 cm. Venation: Parallel. Color: Upper surface: Light violet-blue, 85A, fading to 91A with age. Lower surface: Light violet-blue, 85A, fading to 91A with age.

*Petals.*—Quantity: Five. Shape: Oblong. Tips: Cuspidate.

*Flower throat.*—Appearance: Whiskered. Length: About 8 mm. Diameter: About 2 mm. Color: Throat opening: Green-yellow, 154A, with purple, 86A, venation. Lower surface: 152B.

*Sepals.*—Quantity: Two. Shape: Oblong. Size: Length: About 1.2 cm. Width: About 4 mm. Color: Greener than 146A.

*Reproductive organs.*—Gynoecium: Ovary color: Light green. Style length: About 7.5 mm. Style color: Distal end, light green, proximal, whitish. Stigma: Deltoid with fine white hairs, bent at a 90° angle to style. Androecium: Filaments: Quantity: 5. Length: About 4 mm. Color: Whitish green. Anthers: Length: About 1 mm. Color: Golden yellow.

Disease resistance: The new Scaevola has not been observed to be more resistant to pathogens common to Scaevolas.

Seed production: Seed production has not been observed.

It is claimed:

1. A new and distinct Scaevola plant named 'Sunfan', as illustrated and described.

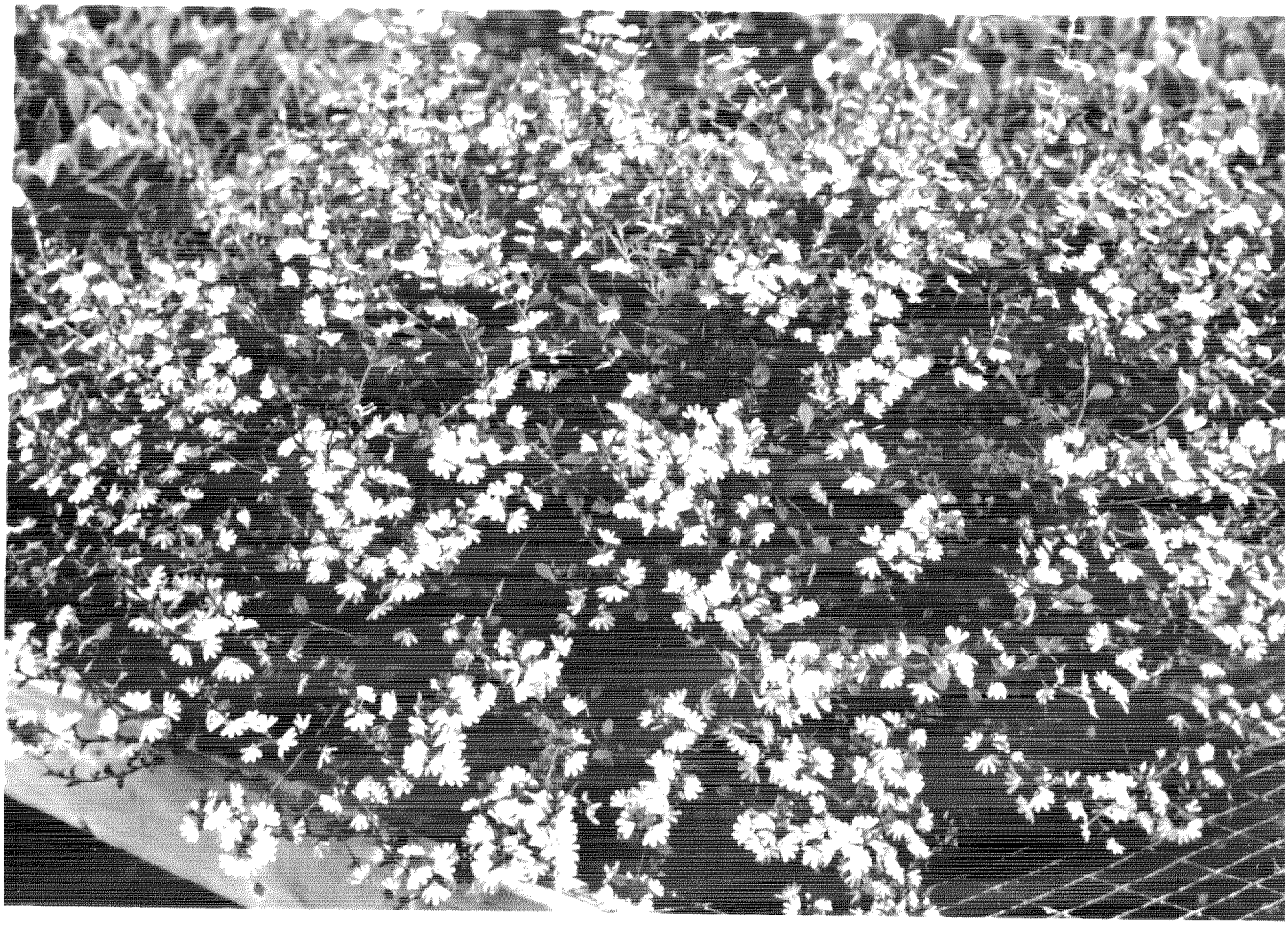

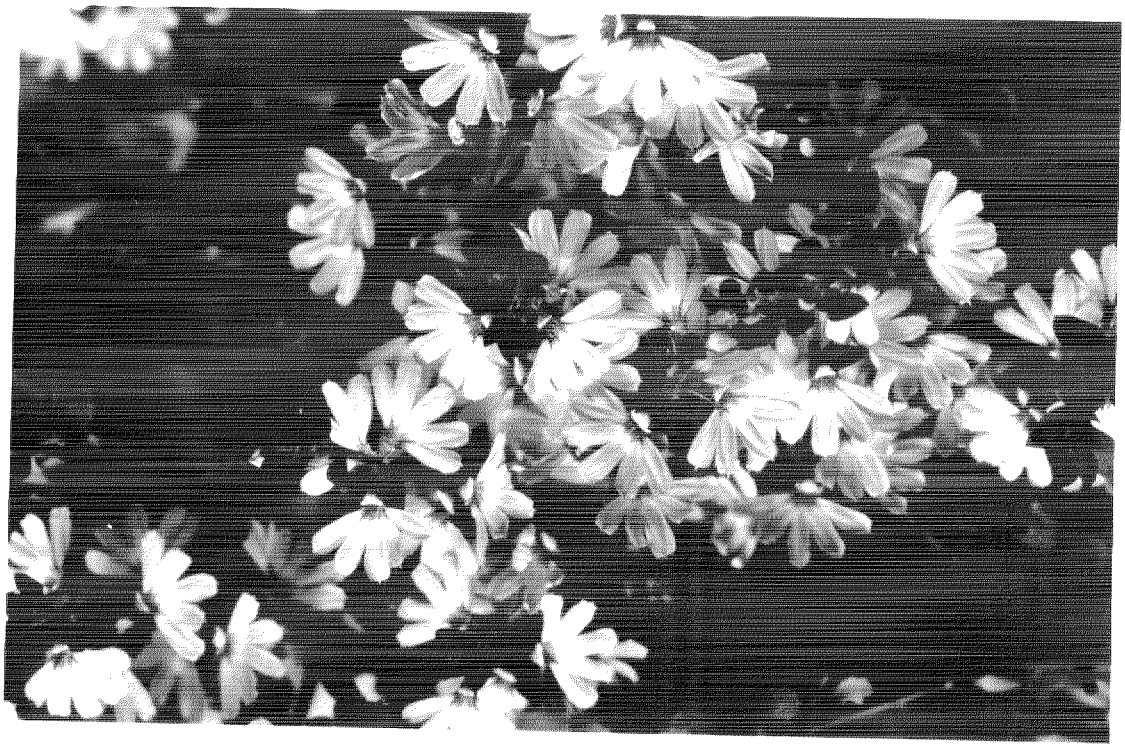

* * * * *